United States Patent
Gómez et al.

(10) Patent No.: US 12,232,807 B2
(45) Date of Patent: *Feb. 25, 2025

(54) METHODS, DEVICES, AND SUPPORT STRUCTURES FOR ASSEMBLING OPTICAL FIBERS IN CATHETER TIPS

(71) Applicant: Medlumics S.L., Madrid (ES)

(72) Inventors: Sara Mas Gómez, Tres Cantos (ES); Juan Sancho Dúra, Tres Cantos (ES); David González Villar, San Sebastián de los Reyes (ES); Matthieu Duperron, Madrid (ES); Carlos Sanz Moreno, Madrid (ES); Alexandre Romoscanu, Geneva (CH); Jorge H. Jiménez, Atlanta, GA (US)

(73) Assignee: Medlumics S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/686,873

(22) Filed: Mar. 4, 2022

(65) Prior Publication Data
US 2022/0280235 A1 Sep. 8, 2022

(30) Foreign Application Priority Data

Mar. 4, 2021 (EP) .................................... 21382179

(51) Int. Cl.
*A61B 18/20* (2006.01)
*A61B 18/24* (2006.01)
(Continued)

(52) U.S. Cl.
CPC .... *A61B 18/24* (2013.01); *A61B 2018/00577* (2013.01); *A61B 2018/2211* (2013.01); *A61B 2018/2266* (2013.01)

(58) Field of Classification Search
CPC .......... A61B 18/20; A61B 18/24; A61N 5/06; A61F 9/008; A61C 1/0046
See application file for complete search history.

(56) References Cited

U.S. PATENT DOCUMENTS

| | | | |
|---|---|---|---|
| 5,290,275 A | | 3/1994 | Kittrell et al. |
| 5,454,782 A | * | 10/1995 | Perkins .................. A61B 18/24 606/17 |

(Continued)

FOREIGN PATENT DOCUMENTS

| | | |
|---|---|---|
| CA | 3083870 A1 | 6/2019 |
| EP | 2120758 A2 | 11/2009 |

(Continued)

OTHER PUBLICATIONS

Boppart, Stephen A., et al., "Real-Time Optical Coherence Tomography for Minimally Invasive Imaging of Prostate Ablation," Computer Aided Surgery 6:94-103, Accepted Feb. 2001, published Online Jan. 2010; 10 pages.

(Continued)

*Primary Examiner* — Lynsey C Eiseman
(74) *Attorney, Agent, or Firm* — Sterne, Kessler, Goldstein & Fox P.L.L.C.

(57) ABSTRACT

A catheter includes proximal and distal sections, a shaft coupled between the proximal and distal sections, and optical fibers extending through the shaft and to the distal section of the catheter. The distal section includes a support structure that includes a proximal end, a distal end, reflective elements, and a cap disposed over a portion of the distal end of the support structure. The proximal end includes alignment receptacles. Each of the optical fibers is inserted into corresponding ones of the alignment receptacles and the alignment receptacles are shaped to maintain the optical fibers straight in the support structure. The distal end includes orifices facing different directions. Each of the (Continued)

optical fibers is optically aligned with corresponding ones of the lenses, reflective elements, and orifices such that the optical fibers in the support structure are straight. The cap includes optical ports aligned with the orifices.

12 Claims, 14 Drawing Sheets

(51) Int. Cl.
  *A61B 18/00* (2006.01)
  *A61B 18/22* (2006.01)

(56) References Cited

U.S. PATENT DOCUMENTS

| | | | |
|---|---|---|---|
| 5,947,977 | A | 9/1999 | Slepian et al. |
| 6,056,745 | A | 5/2000 | Panescu et al. |
| 10,779,904 | B2 | 9/2020 | Ransbury et al. |
| 11,331,142 | B2 | 5/2022 | Sancho Dura et al. |
| 2001/0031942 | A1 | 10/2001 | Tollner et al. |
| 2003/0208252 | A1 | 11/2003 | O'Boyle et al. |
| 2006/0229515 | A1 | 10/2006 | Sharareh et al. |
| 2007/0078500 | A1* | 4/2007 | Ryan ............... A61B 5/6853 600/473 |
| 2007/0270792 | A1 | 11/2007 | Hennemann et al. |
| 2007/0287998 | A1 | 12/2007 | Sharareh et al. |
| 2008/0089641 | A1 | 4/2008 | Feldchtein |
| 2009/0018393 | A1 | 1/2009 | Dick et al. |
| 2009/0306520 | A1 | 12/2009 | Schmitt et al. |
| 2009/0319008 | A1* | 12/2009 | Mayer ............... A61N 5/0624 607/90 |
| 2010/0041986 | A1* | 2/2010 | Nguyen ............ A61B 18/1492 606/33 |
| 2010/0046953 | A1 | 2/2010 | Shaw et al. |
| 2011/0028967 | A1 | 2/2011 | Rollins et al. |
| 2011/0144524 | A1 | 6/2011 | Fish et al. |
| 2012/0265184 | A1 | 10/2012 | Sliwa et al. |
| 2013/0261613 | A1* | 10/2013 | Norris ............... A61B 5/0084 606/14 |
| 2013/0317572 | A1* | 11/2013 | Zhu .................. A61N 1/0551 607/89 |
| 2014/0052126 | A1 | 2/2014 | Long et al. |
| 2014/0171936 | A1 | 6/2014 | Govari et al. |
| 2015/0209105 | A1 | 7/2015 | Margallo Balbas et al. |
| 2015/0359593 | A1 | 12/2015 | Fiser et al. |
| 2016/0038031 | A1 | 2/2016 | Margallo Balbas et al. |
| 2017/0014202 | A1* | 1/2017 | Ransbury ............ A61B 90/37 |
| 2017/0202619 | A1 | 7/2017 | Lim |
| 2018/0168729 | A1 | 6/2018 | Pratten et al. |
| 2018/0214202 | A1 | 8/2018 | Howard et al. |
| 2018/0368703 | A1 | 12/2018 | Franjic et al. |
| 2020/0406010 | A1* | 12/2020 | Massimini ......... A61M 25/0133 |
| 2021/0045834 | A1 | 2/2021 | Ransbury et al. |

FOREIGN PATENT DOCUMENTS

| | | |
|---|---|---|
| EP | 2208475 A1 | 7/2010 |
| EP | 2361549 A2 | 8/2011 |
| EP | 2208475 B1 | 9/2011 |
| EP | 2736434 A1 | 6/2014 |
| EP | 3141181 A1 | 3/2017 |

OTHER PUBLICATIONS

Bouchard, Richard, et al. "Photoacoustic characterization of radiofrequency ablation lesions." Photons Plus Ultrasound: Imaging and Sensing 2012. Vol. 8223. International Society for Optics and Photonics, 2012. 10 pages.

De Boer, Johannes F., et al., "Two-Dimensional Birefringence Imaging In Biological Tissue Using Polarization Sensitive Optical Coherence Tomography," SPIE vol. 3196, 0277, pp. 32-37, Jan. 1998; 6 pages.

Everett, M. J., et al., "Birefringence Characterization of Biological Tissue by Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

González-Suárez, et al., "Relation Between Denaturation Time Measured by Optical Coherence Reflectometry and Thermal Lesion Depth During Radiofrequency Cardiac Ablation: Feasibility Numerical Study," Lasers and Surgery in Medicine, 50(3):222-229, Mar. 2018; 9 pages.

Herranz, D., et al., "Novel Catheter Enabling Simultaneous Radiofrequency Ablation and Optical Coherence Reflectometry," Biomedical Optics Express, 6(9):3268-75, Aug. 2015; 8 pages.

Herranz, D., et al., "Percutaneous RF Ablation Guided by Polarization-Sensitive Optical Coherence Reflectometry in an Integrated Catheter: Experimental Evaluation of the Procedure," Journal of Innovations in Cardiac Rhythm Management, 6(8):2086-91, Aug. 2015; 6 pages.

International Search Report and Written Opinion of the International Searching Authority directed to related international Patent Application No. PCT/EP2021/050603, mailed Apr. 12, 2021; 13 pages.

International Search Report and Written Opinion of the International Searching Authority directed to related international Patent Application No. PCT/EP2021/050604, mailed Apr. 30, 2021; 11 pages.

International Search Report and Written Opinion of the International Searching Authority directed to related international Patent Application No. PCT/EP2021/050602, mailed Apr. 6, 2021; 20 pages.

Iskander-Rizk, Sophinese, et al. "Real-Time Photoacoustic Assessment of Radiofrequency Ablation Lesion Formation in the Left Atrium." Photoacoustics 16 (2019): 100150; 10 pages.

Patel, Nirlep A., et al., "Guidance of Aortic Ablation Using Optical Coherence Tomography," The International Journal of Cardiovascular Imaging 19:171-178, Apr. 2003; 8 pages.

Wittkampf, F., et al., "Electroporation and its Relevance for Cardiac Catheter Ablation," JACC: Clinical Electrophysiology, 4(8):977-986, Aug. 2018; 10 pages.

* cited by examiner

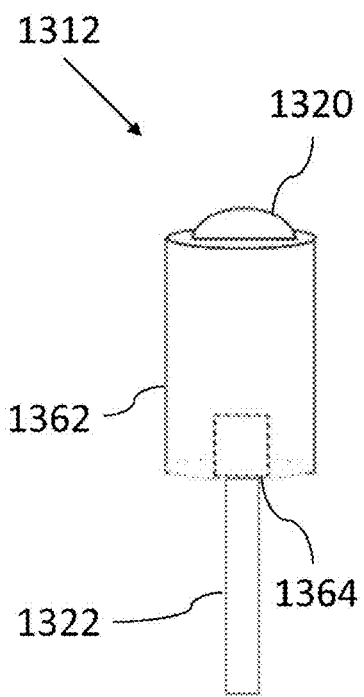
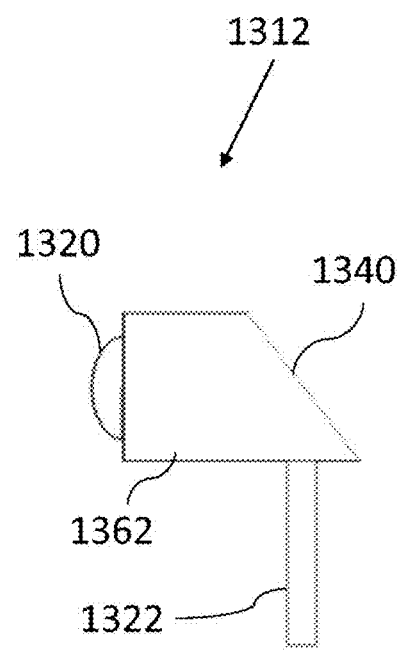
FIG. 13A                FIG. 13B

1420
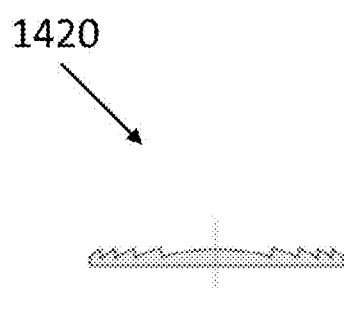
1420'
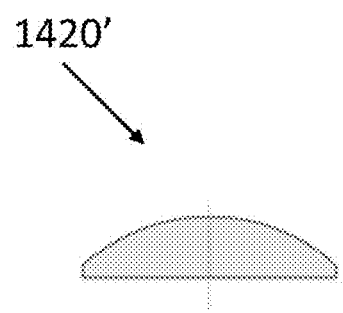
FIG. 14A
FIG. 14B

METHODS, DEVICES, AND SUPPORT STRUCTURES FOR ASSEMBLING OPTICAL FIBERS IN CATHETER TIPS

BACKGROUND

Field

The present disclosure relates to methods, devices, and support structures for assembling optical fibers in catheter tips and facilitating alignment and structural support.

Background

Ablation is a medical technique for producing tissue necrosis. It is used to help treat different pathologies including cancer, Barret's esophagus, or cardiac arrhythmias, among others. For radiofrequency (RF) ablation, the application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen, myosin, or elastin. Traditionally, RF ablation is done by placing an external electrode on the patient's body, and applying an alternating potential to the tip of a catheter that is placed in contact with the tissue to be treated within the patient's body.

In some cases, various energy sources may be utilized for ablation, including cryogenic cooling for cryoablation, radiofrequency, microwave, laser, ultrasound, and the like. In some cases, cryoablation may use extremely cold temperatures for ablating tissue, whereas electroporation ablation may use pulsed electric fields to ablate specific tissue for the treatment of atrial fibrillation.

The ablation effect depends on a number of factors, including applied electrical power, quality of the electrical contact, local tissue properties, presence of blood flow close to the tissue surface, and the effect of irrigation. Because of the variability of these parameters, it may be difficult to obtain consistent results.

Additionally, ablation catheters using optical fibers may provide variable or inconsistent results if optical fibers are not properly and accurately aligned in catheter tips.

BRIEF SUMMARY

Accordingly, there may be a need for providing new methods, devices, and structures for properly aligning optical fibers in catheter tips in order to obtain accurate results.

In the embodiments presented herein, catheters, support structures, and methods are described for assembling and aligning optical fibers in place at catheter tips for use in tissue ablation procedures. In some embodiments, the optical fibers and lenses in the support structure may be affixed in the catheter tip using various methods and devices, as described herein.

In some embodiments, a catheter comprises a proximal section, a distal section, a shaft coupled between the proximal section and the distal section, and optical fibers extending through the shaft and to the distal section of the catheter. The distal section comprises a support structure comprising a proximal end, a distal end, reflective elements, lenses, and a cap disposed over a portion of the distal end of the support structure. The proximal end comprises alignment receptacles. Each of the optical fibers is inserted into corresponding ones of the alignment receptacles and the alignment receptacles are shaped to maintain the optical fibers straight in the support structure. The distal end comprises orifices facing different directions. Each of the optical fibers is optically aligned with corresponding ones of the lenses, reflective elements, and orifices such that the optical fibers in the support structure are straight and have optical access to the exterior of the catheter via the orifices. The cap comprises optical ports aligned with the orifices.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

FIGS. 8A, 8B, 9A, 9B, and 10 illustrate diagrams of example configurations of distal sections of catheters, according to embodiments of the present disclosure.

Figure 11A:
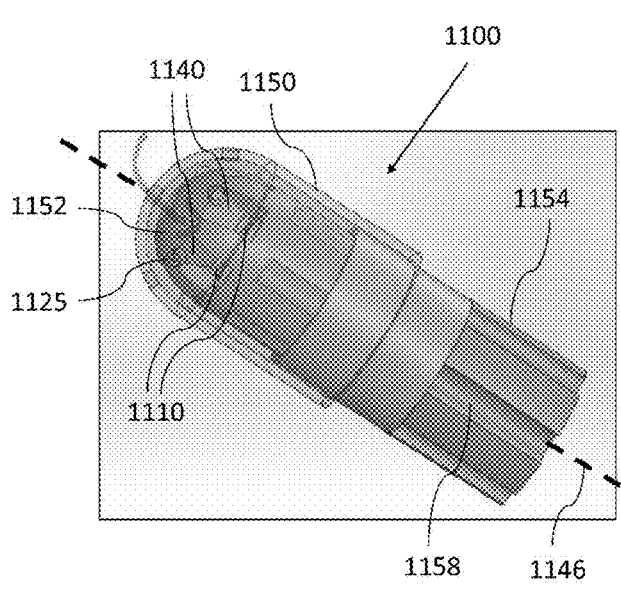
Figure 11B:
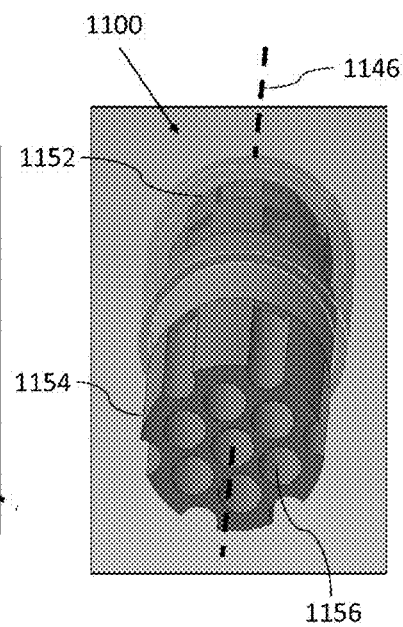

FIGS. 11A and 11B illustrate diagrams of an example support structure, according to embodiments of the present disclosure.

FIGS. 12A, 12B, 12C, 13A, and 13B illustrate diagrams of example optical devices in various arrangements, according to embodiments of the present disclosure.

FIGS. 14A and 14B illustrate diagrams of example lenses, according to embodiments of the present disclosure.

Figure 15:
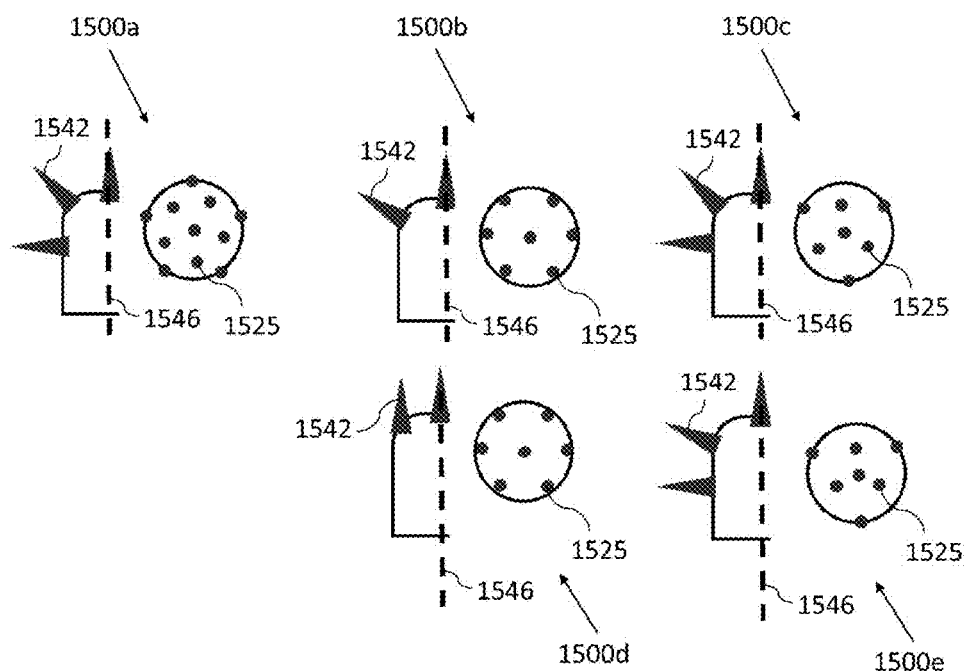

FIG. 15 illustrates diagrams of example arrangements of optical ports at a distal section of a catheter, according to embodiments of the present disclosure.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well, along with additional energy sources for ablation, including but not limited to cryogenic, radiofrequency (RF), microwave, laser, ultrasound, and pulsed electric fields. The principles of using laser energy to treat other pathologies are similar, and therefore the techniques used to apply the laser energy are similar.

Disclosed herein are embodiments of an ablation catheter for merged optical tissue evaluation and laser ablation in which the ablation catheter includes a plurality of optical ports for both evaluating and ablating target tissue. In some embodiments, the plurality of optical ports of the catheter may be configured to transmit beams of exposure radiation to a sample, receive one or more beams of scattered radiation that have been reflected or scattered from the sample, and transmit laser energy such that at least a portion of the sample is ablated. By utilizing the same optical ports for transmission of the optical evaluation signals and the laser ablation signals, the ablation catheter may provide focused evaluation of the same target tissue that is being ablated in a single substrate that allows for both modalities.

Herein, the terms "electromagnetic radiation," "light," and "beam of radiation" are all used to describe the same electromagnetic signals propagating through the various described elements and systems.

Exemplary Catheter Embodiments

Figure 1:
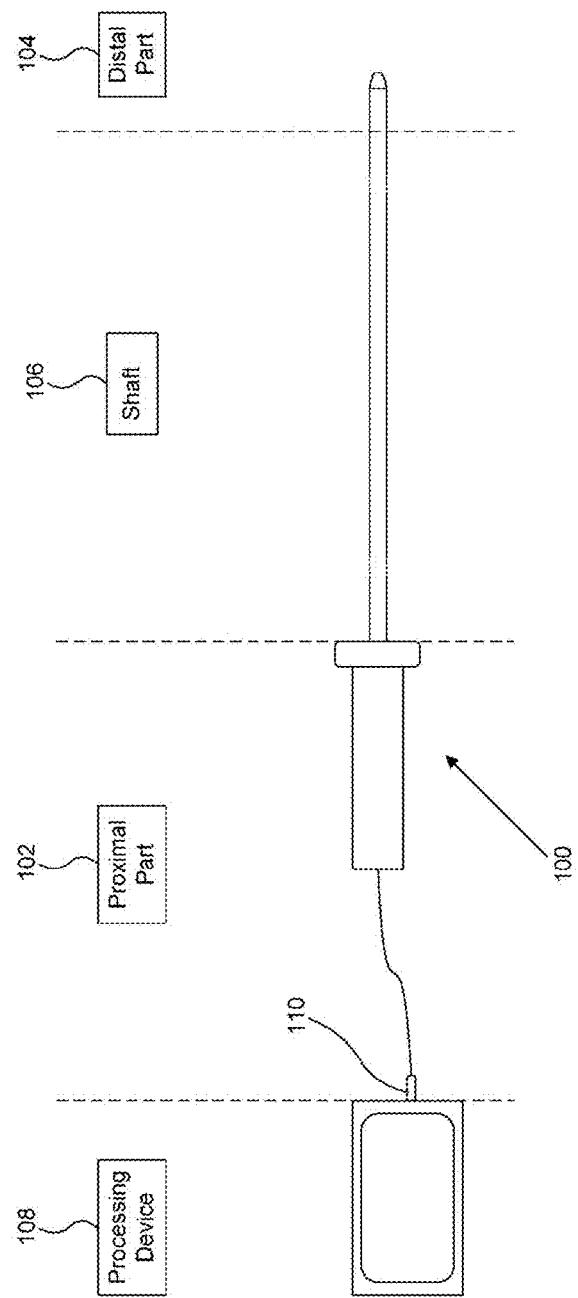
FIG. 1 illustrates an example diagram of a catheter, according to embodiments of the present disclosure.

FIG. 1 illustrates a catheter 100 according to embodiments of the present disclosure. Catheter 100 includes a proximal section 102, a distal section 104, and a shaft 106 coupled between proximal section 102 and distal section 104. In an embodiment, shaft 106 includes one or more radiopaque markers for navigation purposes. In one embodiment, catheter 100 includes a communication interface 110 between catheter 100 and a processing device 108. Communication interface 110 may include one or more one or more optical fibers and connectors between processing device 108 and catheter 100, as described herein. In other examples, communication interface 110 may include an interface component that allows wireless communication, such as Bluetooth, WiFi, cellular, and the like, to communicate with the catheter 100 or other processing components in a catheter system In an embodiment, shaft 106 and distal section 104 are disposable. As such, proximal section 102 may be reused by attaching a new shaft 106 and proximal section 104 each time a new procedure is to be performed. In another embodiment, proximal section 102 is also disposable.

Proximal section 102 may house various electrical and optical components used in the operation of catheter 100. A first optical source may be included within proximal section 102 to generate a source beam of radiation for optical evaluation. The first optical source may include one or more laser diodes or light emitting diodes (LEDs). The beam of radiation generated by the optical source may have a wavelength within the infrared range. In one example, the beam of radiation has a central wavelength of 1.3 µm. The optical source may be designed to output a beam of radiation at only a single wavelength, or it may be a swept source and be designed to output a range of different wavelengths. The generated beam of radiation may be guided towards distal section 104 via the optical transmission medium connected between proximal section 102 and distal section 104 within shaft 106. Some examples of optical transmission media include single mode optical fibers and/or multimode optical fibers. In one embodiment, the electrical transmission medium and the optical transmission medium are provided by the same hybrid medium allowing for both electrical and optical signal propagation.

Furthermore, proximal section 102 may include a second optical source, such as a laser energy source, to generate laser energy that is applied at distal section 104 for tissue ablation. In some embodiments, the laser energy source may emit an ablation beam of laser energy at a wavelength of 980 nm or a wavelength of 1060 nm. The laser energy from the source in the proximal section 102 may propagate down the catheter 100 via an optical transmission medium connected between proximal section 102 and distal section 104 within shaft 106, and the laser energy may be output from the distal section 104 of catheter 100 to target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 50 W that is applied to target tissue for 60-90 seconds.

In an embodiment, proximal section 102 includes one or more components of an interferometer in order to perform low coherence interferometry (LCI) using the light generated from the second optical source. Due to the nature of interferometric data analysis, in an embodiment, the optical transmission medium used for guiding the light to and from distal section 104 does not affect the state and degree of light polarization. In another embodiment, the optical transmission medium affects the polarization in a constant and reversible way. In some embodiments, catheter 100 may include an optical circuit with one or more elements configured to conduct optical spectroscopy. In such embodiments, at least part of the optical path may be made up of multi-mode optical transmission media (e.g. multi-mode optical fiber).

Proximal section 102 may include further interface elements with which a user of catheter 100 can control the operation of catheter 100. For example, proximal section 102 may include a deflection control mechanism that controls a deflection angle of distal section 104. The deflection control mechanism may include a mechanical movement of an element on proximal section 102, or the deflection control mechanism may use electrical connections to control the movement of distal section 104. Proximal section 102 may include various buttons or switches that allow a user to control when laser energy is applied at distal section 104, or when the beams of radiation are transmitted from distal section 104, allowing for the acquisition of optical data. In some embodiments, proximal section 102 may include a deflection control mechanism for controlling one or more pull wires that are coupled to the distal section 104. In some embodiments, deflection control mechanism and the one or more pull wires allow for steering of the distal section of catheter 100 in order to maneuver within and target specific tissue regions for ablation.

Distal section 104 includes a plurality of optical view ports. In some embodiments, the plurality of optical view ports may be referred to herein as orifices in the catheter tip. In an embodiment, one or more of the optical view ports are machined into the outer body of distal section 104. The optical view ports are distributed over the outside of distal section 104, resulting in a plurality of distinct viewing directions. In some embodiments, the optical view ports may transmit and collect light (e.g., optical signals) at various angles from the distal section 104. The optical view ports also allow for a plurality of directions (e.g., beam directions) in which laser energy may be directed for tissue ablation through one or more of the optical view ports. In an embodiment, each of the plurality of viewing directions are substantially non-coplanar. The optical view ports may also be designed with irrigation functionality to cool distal section 104 and surrounding tissue during ablation.

Figure 2A:
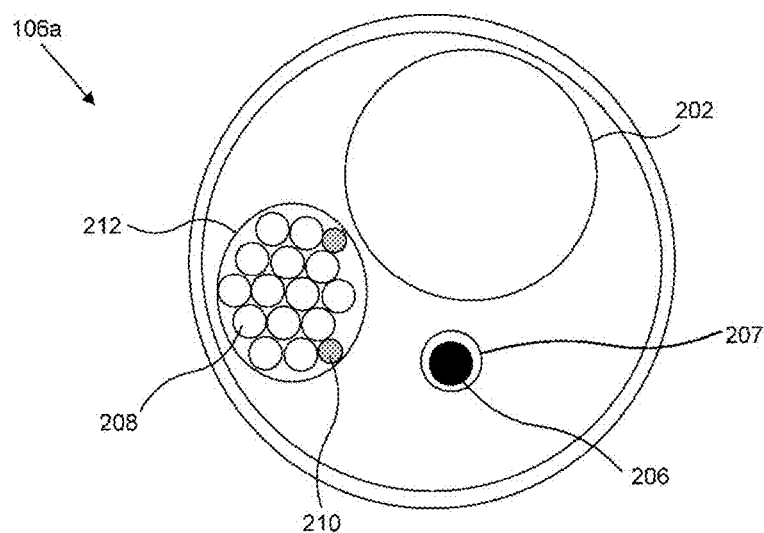
FIGS. 2A and 2B illustrate cross sections of a catheter, according to embodiments of the present disclosure.
Figure 2B:
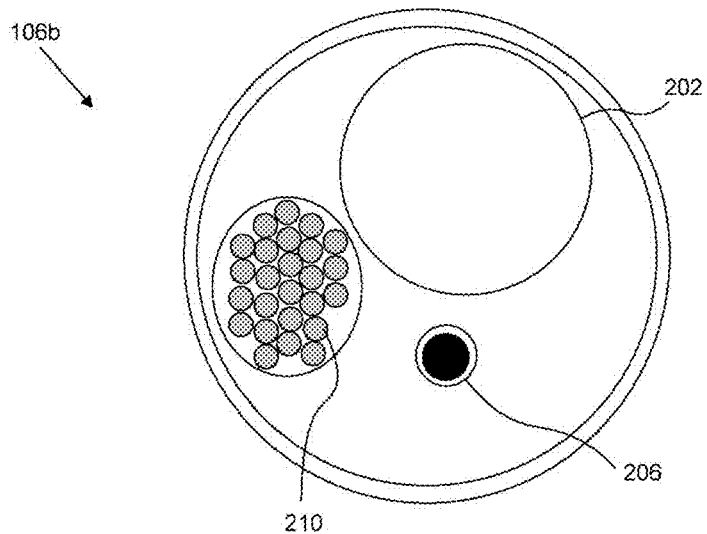

FIGS. 2A and 2B illustrate cross-section views of shaft 106, according to embodiments of the present disclosure. Shaft 106 may include all of the elements interconnecting proximal section 102 with distal section 104. Shaft 106a illustrates an embodiment that houses multiple channels/lumens, including an irrigation channel 202, a cabling channel 212, and a channel for deflection mechanisms 206. Through these channels 207, 212, 202, deflection mechanism 206, electrical connections 208, and optical transmission medium 210, and cooling fluid may be at least partially housed or transported. In some configurations, a protective cover wrapped around both electrical connections 208 and optical transmission media 210 may be used. In other embodiments, optical transmission media 210 and components may be located within a protective cover that is separate from the protective cover in which the electrical connections 208 is housed. Electrical connections 208 may be used to provide signals to optical modulating components located in distal section 104. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions. In some embodiments, the optical transmission medium 210 comprises one or more single mode optical fibers and/or multimode optical fibers.

Irrigation channel 202 may be a hollow tube used to guide cooling fluid towards distal section 104. Irrigation channel 202 may include heating and/or cooling elements disposed along the channel to affect the temperature of the fluid. In another embodiment, irrigation channel 202 may also be used as an avenue for drawing fluid surrounding distal section 104 back towards proximal section 102.

Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an embodiment. This system may be based on a series of aligned and uniformly spaced cutouts in shaft 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other embodiments involving the combination of several control wires attached to the catheter tip may enable the deflection of the catheter tip along different directions.

FIG. 2B illustrates a cross-section of shaft 106b. Shaft 106b depicts an embodiment having most of the same elements as shaft 106a from FIG. 2A, except that there are no electrical connections 208. Shaft 106b may be used in situations where modulation (e.g., multiplexing) of the generated beam of radiation is performed in proximal section 102.

Exemplary Catheter System and Console Embodiments

Figure 3:
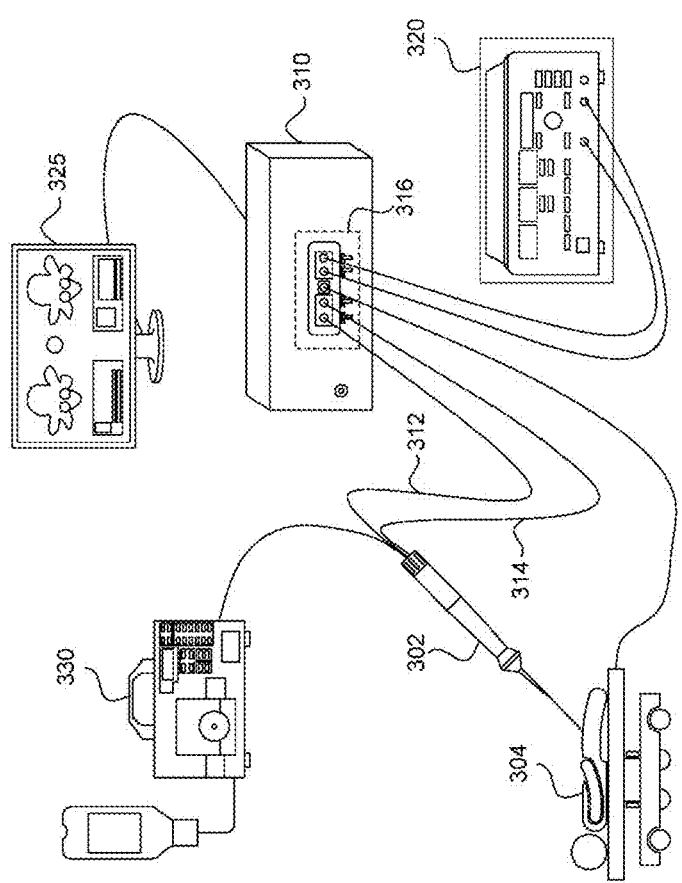
FIG. 3 illustrates a diagram of an example system for ablation, according to embodiments of the present disclosure.

In some embodiments, an ablation catheter and console system described herein uses optical coherence tomography (OCT) and/or optical coherence reflectometry (OCR), refractometry, or other methods to perform tissue ablations, track scar formation in real-time, and monitor/verify lesion geometries and isolation by directly observing the scar pattern in tissue. FIG. 3 illustrates a diagram of an example system 300 for performing ablation according to embodiments of the present disclosure. The system 300 includes catheter 302, console 310, signal generator 320, display 325, and irrigation pump 330. The catheter 302, console 310, signal generator 320, display 325, and irrigation pump 330 may be communicatively coupled together via wired and/or wireless connections. In some embodiments, catheter 302 may represent an exemplary embodiment of catheter 100 shown in FIG. 1. In some embodiments, patient 304 is shown in FIG. 3 for illustrative purposes. It is understood that the embodiments described herein may be used in vivo and/or in vitro.

In some embodiments, catheter 302 may be positioned at a portion of tissue subject to ablation using energy generated by signal generator 320. In some embodiments, signal generator 320 may be an electronic device configured to generate radiofrequency (RF), cryogenic, or electroporation (e.g., pulsed electric field) signals for ablation. The signal generator 320 may be coupled to catheter 302 directly or via the console 310, and may send energy to catheter 302 to ablate the portion of tissue at a selected tissue site. In some embodiments, the portion of tissue may comprise myocardial tissue, cardiac muscle tissue, skeletal tissue, or the like. Energy may be applied to the portion of tissue through optical view ports in the distal section of catheter 302. After applying the energy, structural changes in the tissue may be observed by acquiring optical signals via one or more optical view ports of catheter 302.

Console 310 may comprise a computing device configured to acquire the optical signals from catheter 302 and analyze the optical signals to detect changes in optical properties of the tissue. In some embodiments, console 310 may include hardware (e.g., circuits), firmware, software, or any combination thereof to process the optical signals and perform further analysis. In some embodiments, console 310 may send light through an optical circuit within itself and the catheter 302 and into the tissue to monitor scar progression, contact between the tissue and catheter 302, and other characteristics of the tissue. In some embodiments, console 310 may be referred to herein as a control console, a processing device, and/or controller. Console 310 may be coupled to display 325, which may present results from the optical signal analysis and allow a user to select/view, modify, and/or control parameters related to operation of catheter 302, console 310, signal generator 320, and/or irrigation pump 330.

In some embodiments, irrigation pump 330 may be coupled to catheter 302 via a tubing. In some embodiments, irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation.

In some embodiments, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may include wiring, pins, and/or components used for supplying power and energy from signal generator 320 to catheter 302 for ablation.

In some embodiments, the optical and electrical connections 312, 314 may be connected to console 310 via a communication interface 316. Communication interface 316 may allow for transmission of various signals (e.g., optical and electrical signals) between catheter 302 and console 310. In some embodiments, the communication interface 316 may include a connector that facilitates proper alignment of optical fibers between the catheter 302 and console 310.

Exemplary Catheter Tip, Support Structure, and Optical Fiber Alignment Embodiments Disclosed herein are embodiments of an ablation catheter, including support structures and components for alignment of optical fibers in the distal section of the catheter. By providing such support structures, optical fibers and lenses may be properly aligned and secured in catheter tips to provide efficient optical data of measurements taken during and after ablation.

Figure 4A:
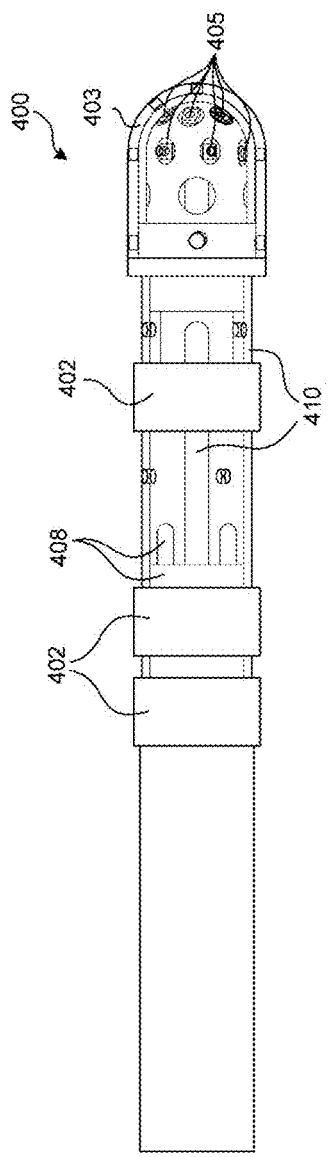
FIG. 4A illustrates a diagram of an example distal section of a catheter, according to embodiments of the present disclosure.

FIG. 4A illustrates a diagram of an example distal section of catheter 400, according to embodiments of the present disclosure. In some embodiments, the distal section of catheter 400 in FIG. 4A may represent an exemplary embodiment of distal section 104 of catheter 100 shown in FIG. 1. The distal section of catheter 400 includes a plurality of electrodes 402, ablation cap 403, a plurality of optical ports 405, one or more pull wire components 408, and irrigation tubing 410. In some embodiments, ablation cap 403 may also be an electrode and may be metallic. In some embodiments, ablation cap 403 may be referred to as a distal cap. In some embodiments, the plurality of optical ports 405 may be referred to herein as a plurality of optical view ports. In some embodiments, the pull wire components 408 may include an anchor and/or other components for allowing steering of the distal section of catheter 400 in order to maneuver within and target specific tissue regions for ablation. In some embodiments, irrigation tubing 410 may allow fluid to be guided along the catheter tip to cool tissue.

Figure 4B:
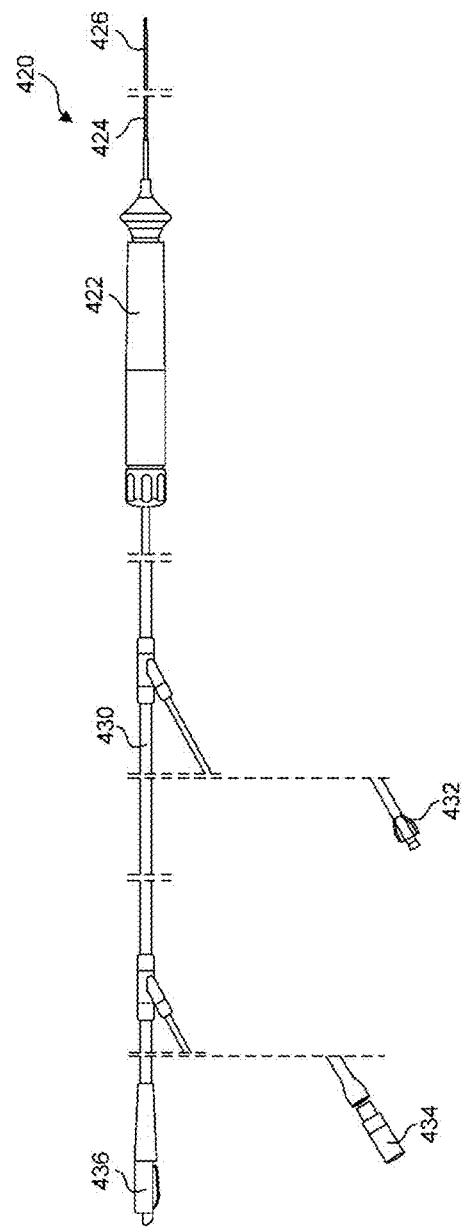
FIG. 4B illustrates a diagram of an example catheter, according to embodiments of the present disclosure.

FIG. 4B illustrates diagram of an example catheter 420, according to embodiments of the present disclosure. In some embodiments, catheter 420 in FIG. 4B may represent an exemplary embodiment of catheter 100 shown in FIG. 1 and the catheter shown in FIG. 4A. Catheter 420 includes handle assembly 422, shaft 424, tip 426, extension line 430, irrigation port 432, connector 434, and connector 436. In some embodiments, connector 434 may be used to connect an electronic device, such as a signal generator for generating energy for ablation (e.g., RF, cryogenic, or electroporation (e.g., pulsed electric field) signals), to the catheter 420. In some embodiments, connector 436 may be a multi-fiber connector that allows a plurality of optical fibers from the console (e.g., console 310) to be coupled to the catheter 420.

In some embodiments, the catheter of FIGS. 4A and 4B may have a single direction or multi-direction steerability. In order to allow for steerability, pull wires (e.g., pull wire components 408) may be connected to the distal section of the catheter (e.g., distal section of catheter 400) and controlled by the catheter's handle (e.g., handle 422). In some embodiments, a thermocouple, electrodes (e.g., electrodes 402), RF wires, and an ablation cap (e.g., ablation cap 403) may be connected to the tip of the catheter (e.g., tip 426). In some embodiments, the ablation cap 403 may include multiple optical ports 405, which may serve as orifices for irrigation and also as optical windows or view ports for light beams from a plurality of optical fibers in the catheter.

In some embodiments, the optical fibers may be directed through the catheter shaft to optical elements (such as lenses and/or reflectors) on the distal section of the catheter. In some embodiments, the optical fibers may be connected to one or more optical elements by wafer-based wave-guide circuits that define the optical components at the catheter tip. In other embodiments, the optical fibers in the catheter tip may connect directly to one or more optical elements, which focus the light into the tissue through the plurality of optical ports 405. In some embodiments, the optical fibers in the catheter tip may be physically separate from one or more optical elements but optically aligned thereto. In some embodiments, multiple optical elements are aligned in an optical path from a distal end of an optical fiber and its corresponding optical port. In some embodiments, the optical elements may be silicon or formed from another optically transparent material. In some embodiments, lenses may also be coated to reduce reflections at interfaces or to allow optical index differences with surrounding tissue, blood, or fluid media.

In some embodiments, the catheter tip may include passive and fixed optics components (e.g., fiber ends and optical elements), without any mechanical switching or scanning devices in the catheter itself. In some embodiments, movement or rotation of optical elements may allow for scanning in different directions in the tissue. In some embodiments, the plurality of optical ports or view ports in the catheter may have various orientations in the catheter tip, in which each output beam directed from each view port in the catheter may face a different direction. For example, one output beam may be directed forward, seven output beams may be directed at 45° with respect to tissue, and seven output beams may be directed at 90° with respect to tissue. In some embodiments, there may be any number of beams, view ports, orientations of the view ports in the catheter tip.

In order to provide precise alignment of the optical fibers with view ports in the catheter tip, disclosed herein are apparatuses, devices, and support structure embodiments for holding fibers and optical elements (such as lenses and/or reflectors) in place at the proper locations in the plurality of view ports in the catheter tip. In some embodiments, a support structure may be provided in the catheter tip to hold optical fibers and corresponding optical elements in proper locations and direct beams exiting the optical fibers in the appropriate directions. In some embodiments, the support structure may also help secure a cap (e.g., ablation cap 403) in place at the catheter tip and direct irrigation flow in the catheter. Additionally, the support structure, in some embodiments, may facilitate in the electrical conduction of energy from a generator wire (e.g., coupled through connector 434 for generating energy for ablation from a signal generator) to the cap of the catheter tip. In some embodiments, the support structure may include orifices also known as alignment orifices to hold the lenses in place, and measured tolerances between the alignment orifices and the optical elements may ensure correct positioning. In some embodiments, the support structure may be electropolished or surface-treated to reduce friction, to allow easier placement of optical fibers during assembly.

In some embodiments, the support structure may be constructed from a single component or multiple components to facilitate assembly. Additionally, in some embodiments, one or more mechanical features may be used to disassemble the different support structure components, fibers, optical elements, and cap. In some embodiments, one or more optical elements may be held in place by the cap to ensure alignment at the optical ports in the cap. In some embodiments, support structures constructed from two components may be aligned using one or more optical elements themselves (e.g., via teeth in between the upper and lower components of the support structure/tip assembly).

Various support structure embodiments for holding fibers and optical elements in place at the proper locations in the catheter tip are shown in the example diagrams of, for example, FIGS. 5-7 and 11.

Figure 5:
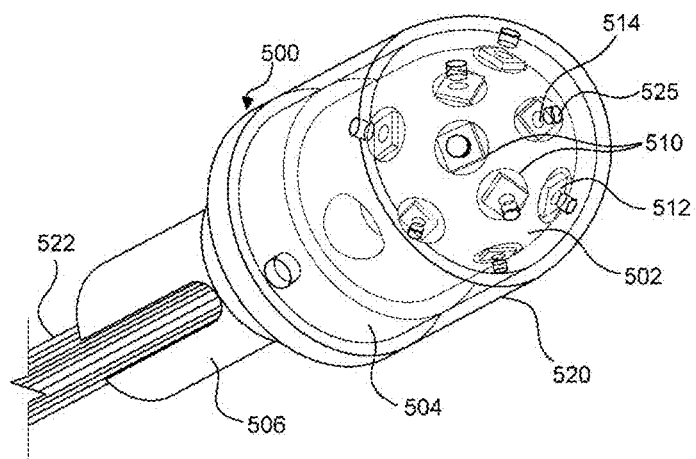
FIG. 5 illustrates a diagram of an example support structure, according to embodiments of the present disclosure.

FIG. 5 illustrates a diagram of an example support structure 500, according to embodiments of the present disclosure. Support structure 500 includes a distal end 502, a body 504, and proximal end 506. The distal end 502 includes a plurality of orifices 510, in which each orifice includes a corresponding optical element 512 of a plurality of optical elements 512 used in a catheter. In some embodiments, optical fibers 522 may represent a bundle of optical fibers optically coupled to the optical elements 512. In some embodiments, a plurality of lenses 514 may be affixed at each orifice 510 using adhesive materials such as a glue, epoxy, or the like.

In some embodiments, a cap 520 may be attached over the distal end 502 of the support structure 500. The cap 520 may include a plurality of optical ports 525. In some embodiments, locations of the optical ports 525 may be aligned with locations of the plurality of lenses 514 in the orifices 510 in the distal end 502. In some embodiments, alignment of the orifices may allow for transmission of optical signals through the optical fibers 522, optical elements 512, and lenses 514 to and from tissue, without interference from the support structure components/materials. In some embodiments, the cap 520 may be disposed over a portion of the distal end 502. Optical ports 525 may be aligned with the orifices 510.

Figure 6:
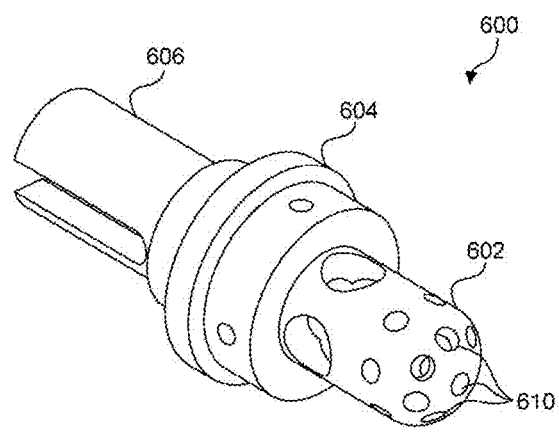
FIG. 6 illustrates a diagram of an example support structure with a unibody, according to embodiments of the present disclosure.

FIG. 6 illustrates diagram of an example support structure 600 with a unibody, according to embodiments of the present disclosure. In some embodiments, the support structure 600 shown in FIG. 6 may be manufactured as a single unibody component. In some embodiments, FIG. 6 illustrates the support structure 600 without any optical fibers or optical elements attached for illustrative purposes. Support structure 600 may include a distal end 602, a body 604, and a proximal end 606. The distal end 602 may include a plurality of orifices 610. While only three orifices 610 are labeled for illustrative purposes, it is understood that there may be any number of orifices 610 in the distal end 602 of the support structure 600.

Figure 7:
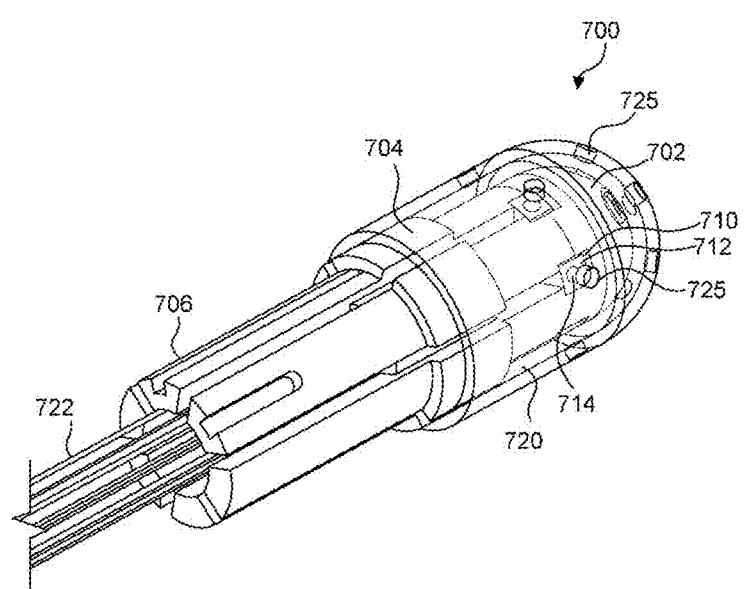
FIG. 7 illustrates a diagram of an example support structure, according to embodiments of the present disclosure.

FIG. 7 illustrates a diagram of an example support structure 700, according to embodiments of the present disclosure. Support structure 700 includes a distal end 702, a body 704, and proximal end 706. The distal end 702 includes a plurality of orifices 710, in which each orifice includes a corresponding optical device 712 of a plurality of optical devices 712 and a lens in a plurality of lenses 714 affixed to each optical device. In some embodiments, optical fibers 722 may represent a bundle of optical fibers. In some embodiments, FIG. 7 also illustrates a cap 720 disposed over the distal end 702 of the support structure 700, in which the cap includes optical ports 725.

Some approaches for coupling optical fibers to optical ports in the catheter tip result in the optical fibers being bent within the optical tip. However, bending optical fibers may create additional complexities. For example, bends can create fiber stress, which may increase risk of breakages and compromise long term durability. Additionally, the assembly process for bending the optical fibers may be more complex, custom fibers (which are typically more expensive) may be needed, or the like. The present disclosure provides embodiments that minimize bending of optical fibers at a distal section of a catheter, thus avoiding such complexities.

Figures 8A, 8B:
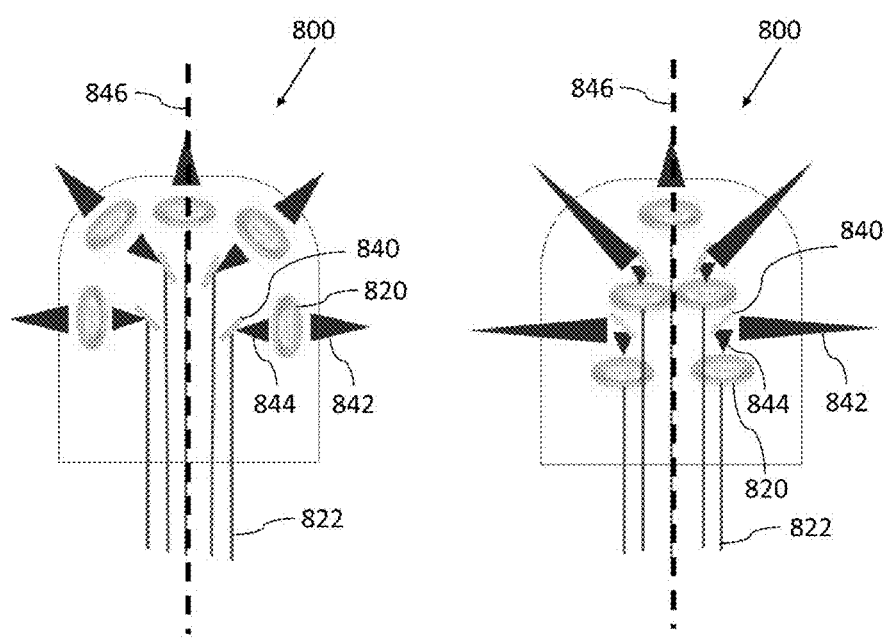

FIGS. 8A and 8B illustrate diagrams of an example distal section of a catheter 800, according to embodiments of the present disclosure. It should be appreciated that, in some embodiments, distal section of the catheter 800 may include structures and functions of distal section of the catheters described in reference to other figures of the present disclosure. For example, though not shown specifically in FIGS. 8A and 8B, the distal section of the catheter 800 may include a support structure (see e.g., FIGS. 5-7, 11) for affixing various optical elements in place.

In some embodiments, the catheter 800 may further include lenses 820, optical fibers 822, and reflective elements 840. Arrows 842 indicate radiation that exits to the exterior of the catheter 800. Arrows 844 indicate the respective optical path between the end of each optical fiber and the exterior of the catheter 800. An optical axis 846 is defined along the length of the distal end of the catheter 800. Each of the optical fibers 822 is optically aligned with corresponding ones of the lenses 820, reflective elements 840, and orifices (not shown; see e.g., orifices 610 (FIG. 6)), such that the optical fibers 822 are straight (e.g., parallel to the optical axis 846) and have optical access to the exterior of the catheter 800 via the orifices. Maintaining the optical fibers in a straight configuration reduce or eliminate complexities associated with bent optical fibers.

FIG. 8A represents an arrangement in which the reflective elements 840 are provided in between the optical fibers 822 and the lenses 820. That is, light passing through lenses 820 may be directed by reflective elements 840 before entering optical fibers 822. FIG. 8B represents an arrangement in which the lenses 820 are provided in between the optical fibers 822 and the reflective elements 840. That is, light entering optical fibers 822 may be directed by reflective elements 840 before passing through the lenses 820. In this manner, bending the optical fibers 822 may be avoided and complexities relating to bent fibers may be avoided.

Figure 9A:
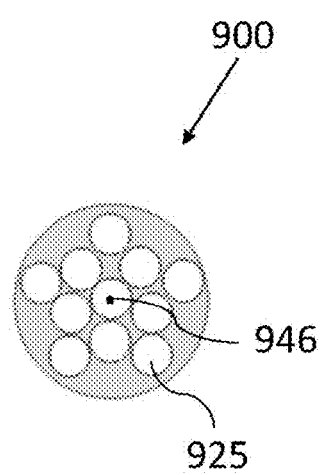
Figure 9B:
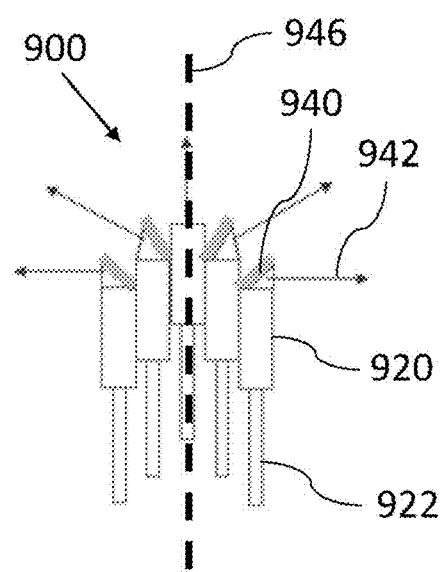

FIGS. 9A and 9B illustrate diagrams of an example distal section of a catheter 900, according to embodiments of the present disclosure. It should be appreciated that, in some embodiments, distal section of the catheter 900 may include structures and functions of distal section of the catheters described in reference to other figures of the present disclosure. For example, though not shown specifically in FIGS. 9A and 9B, the distal section of the catheter 900 may include a support structure (see e.g., FIGS. 5-7, 11) for affixing various optical elements in place.

FIG. 9A presents a head-on view of the distal end of the catheter 900. That is, an optical axis 946 of the distal end of the catheter 900 is oriented in/out of the page. The distal end of the catheter 900 may include optical ports 925. The optical ports 925 may have structures and functions similar to those described in reference to optical ports in other figures.

FIG. 9B presents an interior side view of the distal end of the catheter 900. For reference, the optical axis 946 of the distal end of the catheter 900 is oriented on the plane of the page. For clarity, some catheter structures are not shown (e.g., support structure, cap, or the like), but it should be appreciated that such structures can be implemented as described in reference to other figures. In some embodiments, the catheter 900 may include lenses 920, optical fibers 922, and reflective elements 940. Arrows 942 indicate radiation that exits to the exterior of the catheter 900. It should be appreciated that illumination may also enter catheter 900 along the reverse optical path. Each of the optical fibers 922 is optically aligned with corresponding ones of the lenses 920, reflective elements 940, and optical ports 925 such that the optical fibers 922 are straight and have optical access to the exterior of the catheter 900 via the optical ports 925. It be appreciated that an optical fiber and lens arrangement positioned along the optical axis 946 may omit reflective elements to allow light to enter/exit the catheter 900 along optical axis 946.

Figure 10:
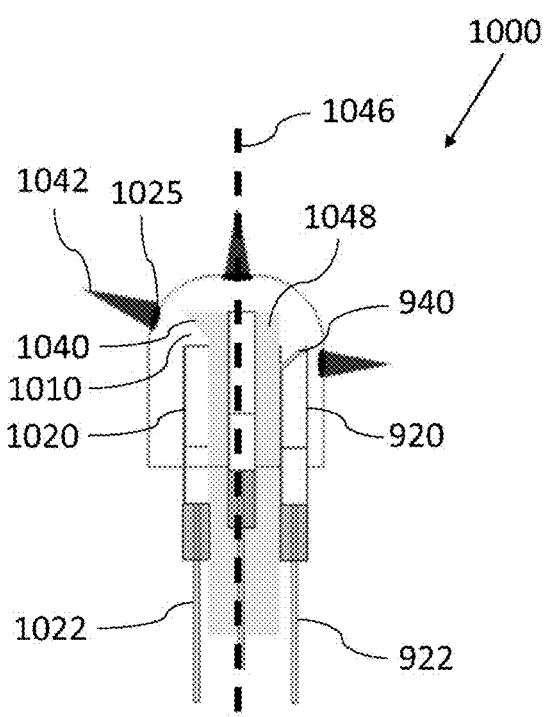

FIG. 10 illustrates a diagram of an example distal end of a catheter 1000 showing different arrangements of optical elements, according to embodiments of the present disclosure. It should be appreciated that, in some embodiments, distal end of the catheter 1000 may include structures and functions of a distal end of the catheters described in reference to other figures of the present disclosure.

In FIG. 10, an optical axis 1046 of the distal end of the catheter 1000 is oriented in the plane of the page. In some embodiments, the distal end of the catheter 1000 may include a support structure 1048, optical ports 1025, lenses 1020, optical fibers 1022, and reflective elements 1040. The optical ports 1025 may have structures and functions similar to those described in reference to optical ports in other figures. The support structure 1048 may include orifices 1010. Arrows 1042 indicate radiation that exits to/enters from the exterior of the catheter 1000. Each of the optical fibers 1022 is optically aligned with corresponding ones of the lenses 1020, reflective elements 1040, orifices 1010, and optical ports 1025 such that the optical fibers 1022 in the support structure 1048 are straight while still having optical access to the exterior of the catheter 1000 via the orifices 1010 and the optical ports 1025.

In some embodiments, the reflective elements 1040 may be integrated into the support structure 1048. For example, a facet can be fabricated onto the body of the support structure 1048. The facet may reflect light. In some embodiments, the reflective elements are not integrated into the body of the support structure 1048, but rather arranged as described in reference to FIG. 9. Corresponding reflective element 940, lens 920, and optical fiber 922 is shown in FIG. 10. Reflective element 940 may be a mirror, a prism surface, a faceted lens surface, or the like. It should be appreciated that arrangements of one type may be used (for example, as in FIG. 9) or arrangements may be combined, as in FIG. 10. It should also be appreciated that an optical fiber and lens arrangement positioned along the optical axis 1046 may omit reflective elements to allow light to enter/exit the catheter 1000 along optical axis 1046.

FIGS. 11A and 11B illustrate diagrams of an example support structure 1100, according to embodiments of the present disclosure. FIG. 11A provides a perspective view of the support structure 1100. An optical axis 1146 of the distal end of the catheter is provided for reference. In some embodiments, the support structure 1100 may include reflective elements 1140, orifices 1110, and irrigation channels 1158. A cap 1150 may be disposed over a distal end 1152 of the support structure 1100. The cap 1150 may include optical ports 1125. The optical ports 1125 may have structures and functions similar to those described in reference to optical ports in other figures. The orifices 1110 (along with their corresponding optical ports) may face different directions, thereby allowing a catheter that uses support structure 1100 to have a wide field of view. The irrigation channels 1158 may be used to clean biological material (e.g., tissue, blood, or the like) to improve optical visibility.

FIG. 11B provides a different perspective view of support structure 1100. A proximal end 1154 of the support structure 1100 may include alignment receptacles 1156. The alignment receptacles 1156 may receive optical fibers (e.g., optical fiber 1022 (FIG. 10)). Each of the optical fibers may be threaded through corresponding ones of the alignment receptacles 1156. The alignment receptacles 1156 are shaped to maintain the optical fibers straight in the support structure, thereby mitigating complexities due to bending of the optical fibers.

In some embodiments, manufacturing the reflective elements 1140 on the support structure 1100 allows different orders of assembly sequences when assembling a catheter tip. For example, the cap 1150 can be welded to a body of the support structure first, before introducing optical fibers through the alignment receptacles 1156.

In some embodiments, the orifices 1110 may be located at different radial locations in the distal end 1152 of the support structure 1100. In some embodiments, the orifices 1110 and the optical ports 1125 are configured such that each corresponding lens faces a different direction and/or angle.

In some embodiments, the optical fibers threaded through the alignment receptacles 1156 may be affixed to the support structure 1100 using an adhesive material. In some embodiments, the support structure 1100 may be a unibody. In some embodiments, the support structure 1100 may be two components that are assembled together (e.g., the distal end 1152 and the proximal end 1154 are two components that are brought together).

Figure 12A:
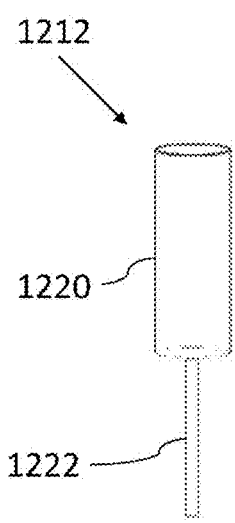
Figure 12B:
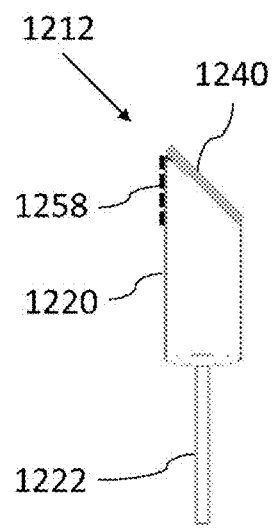
Figure 12C:
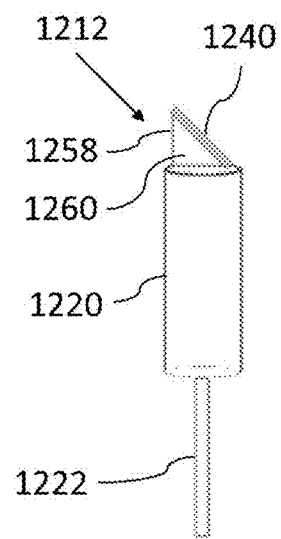

FIGS. 12A, 12B, and 12C illustrate diagrams of an example optical device 1212 in various arrangements, according to embodiments of the present disclosure. In some embodiments, the optical device 1212 comprises a lens 1220 and an optical fiber 1222. The optical device 1212 may also include a reflective element 1240 (e.g., a micromirror) and/or a prism 1260 (e.g., a microprism). In embodiments where the optical device 1212 includes a prism 1260, the reflective element 1240 may be a surface of the prism 1260. The optical device 1212 may be implemented in any of the distal sections of catheters and supported by any of the support structures disclosed herein. While the optical fiber is shown coupled to lens 1220 in each of FIGS. 12A, 12B, and 12C, a person of skill in the art will understand that the lens 1220 may be physically separate from optical fiber 1222, such as when the naked end of the optical fiber 1222 is simply held in place by a receptacle in the support structure, with the lens located along the optical path.

In some embodiments, the lens 1220 may include a gradient-index (GRIN) lens. GRIN lenses or silicon-based lenses may interact with saline while obtaining a desired beam performance.

Referencing FIG. 12A, in some embodiments the optical device 1212 may omit the reflective element and the prism 1260. The optical fiber 1222 may be coupled to the lens 1220. This arrangement may be implemented with support structures having an integrated reflective element (e.g., as described in reference to FIGS. 10, 11A, and 11B). This arrangement may also be implemented for a fiber positioned along an optical axis of a distal section of a catheter to allow light to enter/exit the catheter along the optical axis.

Referencing FIG. 12B, in some embodiments the optical device 1212 may omit the prism 1260. The optical fiber 1222 may be coupled to the lens 1220. The reflective element 1240 may be coupled to the lens 1220 opposite to the end of optical fiber 1222. The lens 1220 may include an optical surface 1258 to allow light to enter and exit the lens while interacting with reflective element 1240. This arrangement may be implemented with support structures that do not have an integrated reflective element (e.g., as described in reference to FIGS. 9B and 10).

Referencing FIG. 12C, in some embodiments the optical fiber 1222 may be coupled to the lens 1220. The prism 1260 may be coupled to the lens 1220 opposite to the end of the optical fiber 1222. The reflective element 1240 may be coupled to the prism 1260, or may be a surface of the prism 1260. The prism 1260 may include an optical surface 1258 to allow light to enter and exit the lens while interacting with reflective element 1240. This arrangement may be implemented with support structures that do not have an integrated reflective element (e.g., as described in reference to FIGS. 9B and 10).

In some embodiments, reflective element 1240 may be a mirror, a reflective coating, a total internal reflection (TIR) surface of the lens 1220 or prism 1260, or the like.

In some embodiments, lens and optical fiber arrangements can be assembled in advance or during the support body assembly, as well as the micromirror and/or microprisms on top of the lenses. The optical fiber 1222 may be connected to the lens substrate by laser welding (fusion) or glue. A glass spacer or ferrule may be used in between the optical fiber 1222 and the lens 1220. To minimize reflections, fiber-lens tilts may be used or specific coating/glues materials that match refractive indexes. Since embodiments of the present disclosure allow for catheters to implement optical fibers without bends, it is possible to use standard fibers (e.g., diameters approximately 80 to 125 microns.

FIGS. 13A and 13B illustrate diagrams of an example optical device 1312 in various arrangements, according to embodiments of the present disclosure. In some embodiments, the optical device 1312 comprises a lens 1320 and an optical fiber 1322. The optical device 1312 may be implemented in any of the distal sections of catheters disclosed herein and supported by any of the support structures disclosed herein.

In some embodiments, the lens 1320 may be a silicon-based lens. GRIN lenses or silicon-based lenses may interact with saline while obtaining a desired beam performance.

Referencing FIG. 13A, in some embodiments the optical device 1312 may also include a connector body 1362. The connector body 1362 may comprise a ferrule and/or a spacer. The optical fiber 1322 may be coupled to the lens 1320 via the connector body 1362. The connector body 1362 may include a fiber-side feature, such as a columnar receptacle, to allow self-alignment of the fiber to the lens 1320. This arrangement may be implemented, for example, with support structures having an integrated reflective element (e.g., as described in reference to FIGS. 10, 11A, and 11B). This arrangement may also be implemented for an optical fiber positioned along an optical axis of a distal section of a catheter to allow light to enter/exit the catheter along the optical axis.

Referencing FIG. 13B, in some embodiments the optical device 1312 may include a connector body 1362 having a reflective element 1340 integrated therein. The connector body 1362 may be fabricated via wafer etching (e.g., a silicon-based wafer). The etched wafer may include the reflective element 1340 (e.g., a TIR surface). Alternatively, in some embodiments, the reflective element 1340 may be a reflective coating, a micromirror, or the like.

FIGS. 14A and 14B illustrate diagrams of example lenses 1420 and 1420', according to embodiments of the present disclosure. In some embodiments, lens 1420 is a Fresnel lens. In some embodiments lens 1420' is a plano-convex, achromatic lens.

FIG. 15 illustrates diagrams of example arrangements 1500a-e of optical ports 1525 at a distal end of a catheter, according to embodiments of the present disclosure. Each arrangement includes a side view and end view. Arrows 1542 indicate an optical path exterior to the catheter 1000 for corresponding optical ports 1525. In the side views, an optical axis 1546 of the distal end of the catheter is shown for reference, which is oriented on the plane of the page.

Referencing arrangement 1500a, in some embodiments the distal end of the catheter may include eleven optical ports 1525 corresponding to eleven output beams and eleven detection directions. The arrangement 1500a may include one front-looking optical port (center port), five optical ports directed at 45 degrees with respect to the optical axis 1546, and five optical ports directed perpendicularly to the optical axis 1546.

Referencing arrangement 1500b, in some embodiment the distal end of the catheter may include seven optical ports 1525 corresponding to seven output beams and seven detection directions. The arrangement 1500b may include one front-looking optical port and six optical ports directed at 60 degrees with respect to the optical axis 1546.

Referencing arrangement 1500c, in some embodiments the distal end of the catheter may include seven optical ports 1525 corresponding to seven output beams and seven detection directions. The arrangement 1500c may include one front-looking optical port, three optical ports directed at 45 degrees with respect to the optical axis 1546, and three optical ports directed perpendicularly to the optical axis 1546.

Referencing arrangement 1500d, in some embodiments the distal end of the catheter may include seven optical ports 1525 corresponding to seven output beams and seven detection directions. The arrangement 1500d may include one front-looking optical port and six additional front-looking optical ports distributed around the center optical port.

Referencing arrangement 1500e, in some embodiments the distal end of the catheter may include seven optical ports 1525 corresponding to seven output beams and seven detection directions. The arrangement 1500e may include one front-looking optical port, three optical ports directed at 60 degrees with respect to the optical axis 1546, and three optical ports directed perpendicularly to the optical axis 1546.

Embodiments referencing FIG. 15 present non-limiting examples of arrangements of optical port numbers and directions. It should be appreciated that, in some embodiments, other quantities of optical ports and directions may be used. It should also be appreciated that a corresponding number of optical elements may be included in the arrangement. For example, a number of lenses may be implemented that correspond to the number of optical ports.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A catheter comprising:
   a proximal section of the catheter;
   a distal section of the catheter;
   a shaft coupled between the proximal and distal sections of the catheter; and
   optical fibers extending through the shaft and to the distal section of the catheter, wherein the distal section comprises:
   a support structure comprising:
      a proximal end comprising alignment receptacles, wherein each of the optical fibers ends in the support structure and is disposed in a corresponding one of the alignment receptacles, wherein the alignment receptacles are shaped to maintain the optical fibers straight in the support structure such that the optical fibers are unbent within the support structure; and
      a distal end comprising orifices facing different directions;
   reflective elements, each reflective element held in place by the support structure;
   lenses, wherein each of the optical fibers is optically aligned with a corresponding one of the lenses, a corresponding one of the reflective elements, and a corresponding one of the orifices such that the optical fibers in the support structure are straight, and wherein the optical fibers are positioned to send and receive optical signals to and from an exterior of the catheter via the lenses, the reflective elements, and the orifices; and
   a cap disposed over a portion of the distal end of the support structure, wherein the cap comprises optical ports aligned with the orifices.

2. The catheter of claim 1, wherein the optical fibers are affixed to the support structure via adhesive material.

3. The catheter of claim 1, wherein the orifices are located at different radial locations in the distal end of the support structure.

4. The catheter of claim 1, wherein each of the lenses is optically aligned with the corresponding one of the orifices and a corresponding one of the optical ports and faces a different direction.

5. The catheter of claim 1, wherein the support structure is a unibody.

6. The catheter of claim 1, wherein the support structure comprises a first structural part and a second structural part coupled to the first structural part.

7. The catheter of claim 1, wherein the reflective elements are mirrors or prism surfaces.

8. The catheter of claim 1, wherein the corresponding one of the reflective elements is disposed between the corresponding one of the lenses and a corresponding one of the optical fibers.

9. The catheter of claim 1, wherein:
   an optical axis is defined along a length of the distal section of the catheter;
   an optical path is defined by a corresponding one of the optical fibers, the corresponding one of the reflective elements, and the corresponding one of the lenses; and
   the corresponding one of the reflective elements defines an angle in the optical path with respect to the optical axis.

10. The catheter of claim 1, wherein each one of the lenses is physically coupled to an end of a corresponding one of the optical fibers.

11. The catheter of claim 1, wherein each one of the lenses is a GRIN lens.

12. A catheter comprising:
   a proximal section of the catheter;
   a distal section of the catheter;
   a shaft coupled between the proximal and distal sections of the catheter; and
   optical fibers extending through the shaft and to the distal section of the catheter, wherein the distal section comprises:
   a support structure comprising:
      a proximal end comprising alignment receptacles, wherein each of the optical fibers ends in the support structure and is disposed in a corresponding one of the alignment receptacles, wherein the alignment receptacles are shaped to maintain the optical fibers straight in the support structure such that the optical fibers are unbent within the support structure; and
      a distal end comprising orifices facing different directions;
   reflective elements, wherein the reflective elements are faceted surfaces of a body of the support structure;
   lenses, wherein each of the optical fibers is optically aligned with a corresponding one of the lenses, a corresponding one of the reflective elements, and a corresponding one of the orifices such that the optical fibers in the support structure are straight, and wherein the optical fibers are positioned to send and receive optical signals to and from an exterior of the catheter via the lenses, the reflective elements, and the orifices; and a cap disposed over a portion of the distal end of the support structure, wherein the cap comprises optical ports aligned with the orifices.

\* \* \* \* \*